United States Patent
Liu et al.

(10) Patent No.: US 7,381,844 B2
(45) Date of Patent: Jun. 3, 2008

(54) HYDROGENATION PROCESS OF CHLORINATED NITROBENZENE

(75) Inventors: Yu-Chang Liu, Taichung (TW); Chung-Yin Huang, Chiayi (TW); Yu-Wen Chen, Taoyuan County (TW)

(73) Assignee: National Central University, Taoyuan (TW)

( * ) Notice: Subject to any disclaimer, the term of this patent is extended or adjusted under 35 U.S.C. 154(b) by 12 days.

(21) Appl. No.: 11/462,374

(22) Filed: Aug. 4, 2006

(65) Prior Publication Data

US 2008/0033211 A1 Feb. 7, 2008

(51) Int. Cl.
*C07C 209/00* (2006.01)

(52) U.S. Cl. .................. 564/406; 564/416; 564/417

(58) Field of Classification Search ............... None
See application file for complete search history.

(56) References Cited

U.S. PATENT DOCUMENTS

| | | | |
|---|---|---|---|
| 4,140,719 A | | 2/1979 | Tull et al. |
| 4,326,078 A | | 4/1982 | Herrmann |
| 4,551,441 A | * | 11/1985 | Van Dijk et al. ........... 502/159 |

OTHER PUBLICATIONS

Article Titled "The metal complex effect on the selective hydrogenation of m-and p-chloronitrobenzene over PVP-stabilized platinum colloidal catalysts" jointly authored by Tu et al., Journal of Molecular Catalysis A:Chemical 159, 2000 (pp. 115-120).
Article Titled "Hydrogenation of o-chloronitrobenzene over polymer-stabilized palladium-platinum bimetallic colloidal Clusters" jointly authored by Yang et al., Journal of Molecular Catalysis A:Chemical 147, 1999 (pp. 55-62).
Article Titled "Comparisons of Activation Energies for Guest Escapes from the Inner Phases of Hemicarcerands with Varying Numbers of Bowl-linking Groups" jointly authored by Robbins et al., J. Chem. Soc., Chem. Commun., 1995 (pp. 1515-1516).
Article Titled "Hydrogenation of para-chloronitrobenzene over supported ruthenium-based catalysts" jointly authored by Tijani et al., Applied Catalysis, 76, 1991 (pp. 255-266).
Article Titled "Influence of metal.ions on hydrogenation of o-chloronitrobenzene over platinum colloidal clusters" jointly authored by Yang et al., Applied Catalysis A: General 164, 1997 (pp. 197-203).
Article Titled "Pt/γ-AI2O3 catalytic membranes vs. Pt on γ-AI2O3 powders in the selective hydrogenation of p-chloronitrobenzene" jointly authored by Vitulli et al., Catalysis Letters 44, 1997 (pp. 205-210).
Article Titled "Metal complex effect on the hydrogenation of O-chloronitrobenzene over polymer-stabilized colloidal ruthenium clusters" jointly authored by Yan et al., Journal of Molecular Catalysis A: Chemical 170, 2001 (pp. 203-208).

* cited by examiner

*Primary Examiner*—Sikarl A Witherspoon
(74) *Attorney, Agent, or Firm*—Jianq Chyun IP Office

(57) ABSTRACT

A hydrogenation process of chloronitrobenzene. The hydrogenation process comprises the steps of producing a nano-sized boron-containing nickel catalyst, wherein a ratio of the amount of the boron atom to the amount of the nickel atom in the nanosized boron-containing nickel catalyst is of about 0.1-0.9. Then, the nanosized boron-containing nickel catalyst is placed into a reactor with a chloronitrobenzene an alcohol solvent having carbon number less than four per molecule and a hydrogenation process is performed to hydrogenating the chloronitrobenzene in hydrogen with a reaction pressure of about 5-40 atm and a reaction temperature of about 40-150° C.

11 Claims, 1 Drawing Sheet

HYDROGENATION PROCESS OF CHLORINATED NITROBENZENE

BACKGROUND OF THE INVENTION

1. Field of Invention

The present invention relates to a hydrogenation process of chloronitrobenzene. More particularly, the present invention relates to a hydrogenation process of chloronitrobenzene with the use of nanosized boron-containing nickel catalyst.

2. Description of Related Art

Conventionally, the noble metal is used as the catalyst in the liquid-phase hydrogenation process of chloronitrobenzene, wherein the catalyst includes palladium (Pd), platinum (Pt) and ruthenium (Ru). That is, by using the noble metal as the catalyst, the ortho-chloronitrobenzene is hydrogenated into the ortho-chloroaniline, the meta-chloronitrobenzene is hydrogenated into the meta-chloroaniline and the para-chloronitrobenzene is hydrogenated into the para-chloroaniline.

In the Journal of Applied Catalysis (vol. 76, pages 255-266, 1991), Figueras et al. disclose the use of the ruthenium as the reaction catalyst in the hydrogenation process of the ortho-chloronitrobenzene. In addition, Liao et al., in J. Chem. Soc., Chem. Comm. (pages 1155-1156, 1995), described the use of palladium-ruthenium bi-metals as the reaction catalyst in the hydrogenation process of the ortho-chloronitrobenzene. Furthermore, Liu et al., in Applied Catalysis A: General (vol. 164, pages 197-203, 1997), disclosed the use of platinum cluster as the reaction catalyst in the hydrogenation process of the para-chloronitrobenzene. Moreover, in Catalysis Letter (vol. 44, pages 205-210, 1997), Vitulli et al. revealed the use of platinum/aluminum oxide as the reaction catalyst in the hydrogenation process of the ortho-chloronitrobenzene. Also, Liu et al. in J. Molecular Catalysis A: Chemical (vol. 147, pages 55-62, 1999) disclosed the use of palladium-platinum bi-metals as the reaction catalyst in the hydrogenation process of the para-chloronitrobenzene. Further, Liu et al. in J. Molecular Catalysis A: Chemical (vol. 159, pages 115-120, 2000) illustrated the use of platinum mixed with the polyvinyl alcohol surfactant as the reaction catalyst in the hydrogenation process of the ortho-chloronitrobenzene. Liu et al. in J. Molecular Catalysis A: Chemical (vol. 170, pages 203-208, 2001) revealed the use of ruthenium mixed with the polyvinyl alcohol surfactant as the reaction catalyst in the hydrogenation process of the para-chloronitrobenzene.

In addition, in American Patent with the U.S. Pat. No. 4,326,078, the noble metal is used as the reaction catalyst for hydrogenating nitrobenzene to form oxy-azobenzene. Further, American Patent with the U.S. Pat. No. 4,140,719 disclosed the use of the phase-shifting catalyst for fluorinating the 2,4,5-trichloro nitrobenzene to form 2,4-difluoro nitro benzene.

However, the conventional hydrogenation processes mentioned in all the documents and the issued patterns use noble metal such as palladium, platinum and ruthenium as the reaction catalyst. The noble metal is expensive and possesses high hydrogenation ability. Therefore, it is easy to generate byproducts during the hydrogenation process.

SUMMARY OF THE INVENTION

Accordingly, at least one objective of the present invention is to provide a hydrogenation process of chloronitrobenzene with the use of a nanosized boron-containing nickel catalyst. Because of the high activity and high product selectivity of the nanosized boron-containing nickel catalyst, 99% of the product of the hydrogenation process of the chloronitrobenzene is chloroaniline.

At least another objective of the present invention is to provide a method for producing nanosized boron-containing nickel catalyst. The particle of the generated nanosized boron-containing nickel catalyst has small diameter and large surface area so that the generated nanosized boron-containing nickel catalyst possesses high activity and selectivity to desired product.

To achieve these and other advantages and in accordance with the purpose of the invention, as embodied and broadly described herein, the invention provides a hydrogenation process of chloronitrobenzene. The hydrogenation process comprises the steps of producing a nanosized boron-containing nickel catalyst, wherein a ratio of the amount of the boron atom to the amount of the nickel atom in the nanosized boron-containing nickel catalyst is of about 0.1-0.9. Then, the nanosized boron-containing nickel catalyst is placed into a reactor with a chloronitrobenzene, an alcoholic solvent having carbon number less than four per molecule and a hydrogenation process is performed to hydrogenate the chloronitrobenzene in hydrogen gas with a reaction pressure of about 5-40 atm and a reaction temperature of about 40-150° C.

In the present invention, a method for forming the nanosized boron-containing nickel catalyst comprises a step of mixing a nickel salt and a boron hydride with the use of an ethanolic solution. Furthermore, the nickel salt includes nickel acetate, nickel nitrate and nickel chloride and the boron hydride includes potassium borohydride and sodium borohydride. In addition, the nanosized boron-containing nickel catalyst is formed at temperature of about 20-50° C. in an oxygen free environment with filling of nitrogen or hydrogen. Also, the volume concentration of ethanol in the ethanolic solution is about 50%. Moreover, the alcoholic solvent includes methanol, ethanol, proposal and butanol. Further, the structure of nanosized boron-containing nickel catalyst is amorphous type and the diameter of the particle of the nanosized boron-containing nickel catalyst is less than 50 nanometer and the surface area of the particle of the nanosized boron-containing nickel catalyst is greater than 20 $m^2/g$. The chloronitrobenzene includes para-chloronitrobenzene, meta-chloronitrobenzene and ortho-chloronitrobenze.

The present invention also provides a method for producing nanosized boron-containing nickel catalyst. The method comprises steps of providing a nickel salt solution and providing a boron hydride solution. Then, the boron hydride solution is drop by drop added into the nickel salt solution to form a catalyst while the nickel salt solution is stirred at a temperature of about 20-50 centigrade under an oxygen free environment. The catalyst is washed by using de-ionized water and ethanol to form nanosized boron-containing nickel catalyst, wherein the ratio of the amount of the boron atom to the amount of the nickel atom in the nanosized boron-containing nickel catalyst is of about 0.1-0.9.

In the present invention, each particle of the nanosized boron-containing nickel catalyst is amorphous type and the diameter of the particle of the nanosized boron-containing nickel catalyst is less than 50 nanometer and the surface area of the particle of the nanosized boron-containing nickel catalyst is larger than 20 $m^2/g$. Also, the boron hydride includes potassium borohydride and sodium borohydride. In addition, the oxygen free environment is filled with nitrogen or hydrogen. Furthermore, the nickel salt includes nickel acetate, nickel nitrate and nickel chloride.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE PREFERRED EMBODIMENTS

Figure 1:
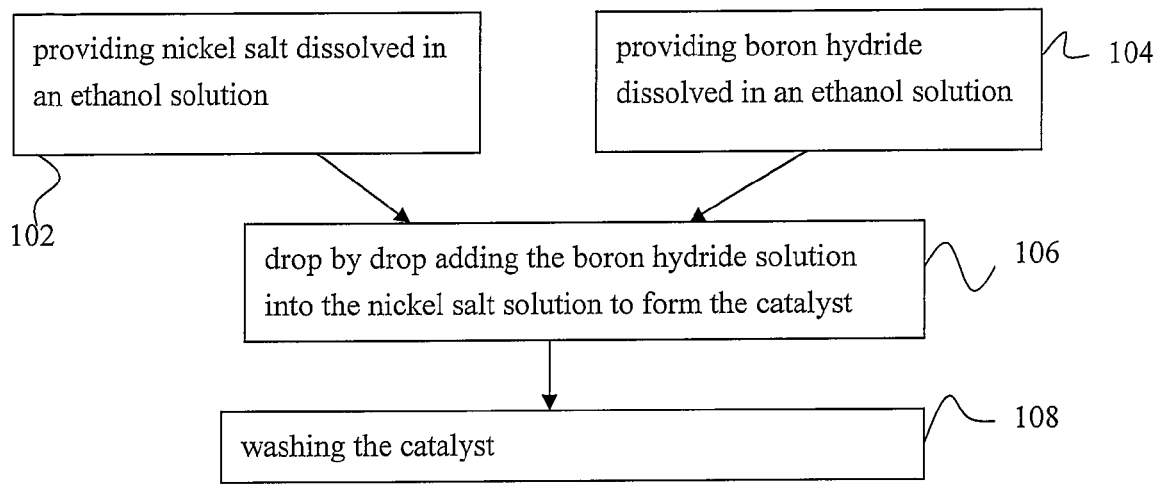
FIG. 1 is a process flow diagram, schematically illustrating a method for producing a nanosized boron-containing nickel catalyst according to the present invention.

In the invention, the chloronitrobenzene is hydrogenated to form chloroaniline with the use of the nanosized boron-containing nickel catalyst. In the formation of the nanosized boron-containing nickel catalyst, under the room temperature in an oxygen free environment, the boron hydride used as a reducing agent is added to the nickel salt with the use of the ethanolic solvent. That is, as shown in FIG. 1, the nickel salt is dissolved in the ethanolic solvent (step 102) and the boron hydride is dissolved in another ethanolic solvent (step 104) respectively, and then the boron hydride solution is drop-by-drop added into the nickel salt solution (step 106). Thereafter, the reaction product, the catalyst, is washed with distilled water (step 108). The composition of the nanosized boron-containing nickel catalyst can be represented by $NiB_x$, wherein x denotes the ratio of the amount of the boron atom to the amount of the nickel atom and x is no less than 0.1 and no larger than 0.9. In addition, each particle of $NiB_x$ is at nanosize scale. That is, the catalyst particle is amorphous with the diameter less than 50 nanometer and surface area no less than 20 $m^2/g$. Notably, the boron hydride can be, for example, sodium borohydride or potassium borohydride. The nanosized boron-containing nickel catalyst is formed under the oxygen free environment with filling of nitrogen or hydrogen. Also, the temperature for preparing the boron-containing nickel catalyst is of about 20-50° C.

Figure 2:
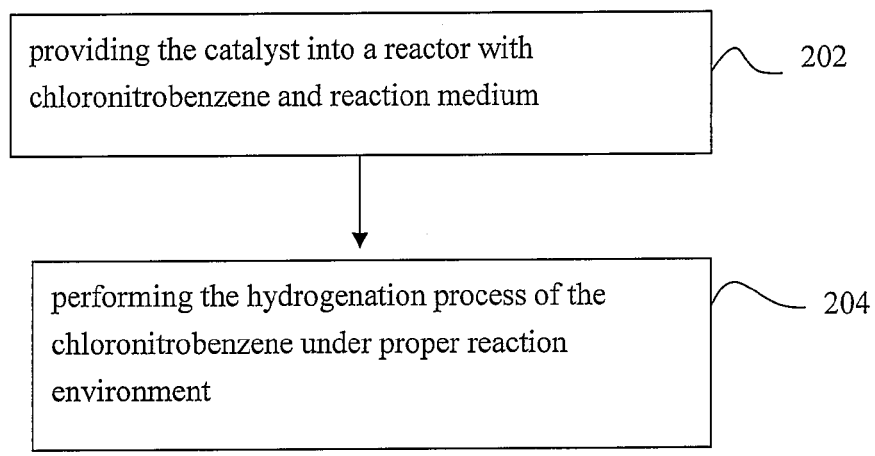
FIG. 2 is a process flow diagram, schematically illustrating a hydrogenation process of chloronitrobenzene with the use of the nanosized boron-containing nickel catalyst according to the present invention.

Thereafter, under hydrogen with the pressure about 5-40 atm and the reaction temperature of about 40-150° C., the hydrogenation process of the chloronitrobenzene is performed in a slurry reactor with an alcoholic solvent having carbon number less than four per molecule and with the use of the nanosized boron-containing nickel catalyst. That is, as shown in FIG. 2, the nanosized boron-containing nickel catalyst is added into the reactor containing the chloronitrobenzene (step 202) and then the hydrogenation process is performed under proper reaction environment (step 204). It should be noticed that the alcoholic solvent can be, for example, methanol or ethanol. Furthermore, the preferred hydrogen pressure for the hydrogenation process is about 5-15 atm and the preferred reaction temperature is about 50-120° C.

Notably, the nanosized boron-containing nickel catalyst formed by using the method provided by the present invention possesses the characteristics of the particle size within the nanometer range, high surface area and amorphous. Therefore, the nanosized boron-containing nickel catalyst has high activity and high product selectivity for performing the hydrogenation process of the chloronitrobenzene. That is, over 99% of the product from the hydrogenation process of the chloronitrobenzene is chloroaniline.

The preferred embodiments of the present invention are recited below for further detail describing the method for preparing the nanosized boron-containing nickel catalyst and the hydrogenation process of the chloronitrobenzene.

First Embodiment

Nickel salt, such as nickel acetate, nickel nitrate and nickel chloride, is dissolved in a 20 ml solution composed of deionized water and ethanol to form a nickel salt solution. Notably, the nickel salt is weighted of about 0.498 g (2 mmole). Furthermore, volume ratio of the deionized water to the ethanol is 1. That is, the solution is composed of 10 ml de-ionized water and 10 ml-99.5% ethanol. Moreover, boron hydride is dissolved in a solution composed of deionized water and ethanol to form boron hydride solution. Notably, the boron hydride, such as sodium borohydride or potassium borohydride, is weighted of about 0.227 g (6 mmole). Furthermore, volume ratio of the deionized water to the ethanol is 1. That is, the solution is composed of 3 ml de-ionized water and 3 ml-99.5% ethanol. Under the zero-centigrade ice bath, the nickel salt solution is stirred with a stirring rate of about 100 rpm while the boron hydride solution is drop-by-drop added into the nickel salt solution by using the peristaltic pump. Therefore, a black-color catalyst is produced. Then, the catalyst is washed by de-ionized water for three times and then by ethanol for twice. As a result, the nanosized boron-containing nickel catalyst is obtained.

Furthermore, the catalyst is an amorphous type and the diameter of the catalyst particle measured by using Transmission Electron Microscopy (TEM) is less than 50 nanometer. In addition, the surface area of the catalyst particle measured by using nitrogen sorption is no less than 20 $m^2/g$.

Second Embodiment

Nickel salt, such as nickel acetate, nickel nitrate and nickel chloride, is dissolved in a 20 ml solution composed of deionized water and ethanol to form a nickel salt solution. Notably, the nickel salt is weighted of about 0.498 g (2 mmole). Furthermore, volume ratio of the deionized water to the ethanol is 1. That is, the solution is composed of 10 ml de-ionized water and 10 ml-99.5% ethanol. Moreover, boron hydride is dissolved in a solution composed of deionized water and ethanol to form boron hydride solution. Notably, the boron hydride, such as sodium borohydride or potassium borohydride, is weighted of about 0.227 g (6 mmole). Furthermore, volume ratio of the deionized water to the ethanol is 1. That is, the solution is composed of 3 ml de-ionized water and 3 ml-99.5% ethanol. At about 20-80° C., the nickel salt solution is stirred with a stirring rate of about 500 rpm while the boron hydride solution is drop-by-drop added into the nickel salt solution by using the peristaltic pump. Therefore, a dark-color catalyst is produced. Then, the catalyst is washed by de-ionized water for three times and then by ethanol for twice. As a result, the nanosized boron-containing nickel catalyst is obtained. In addition, the formation of the nanosized boron-containing nickel catalyst is accomplished in an oxygen free environment by filling with nitrogen or hydrogen at the room temperature. More specifically, the preferred temperature for preparing the boron-containing nickel catalyst is of about 25° C.

Furthermore, the catalyst is an amorphous type and the diameter of the catalyst particle measured by using Transmission Electron Microscopy (TEM) is less than 50 nanometer. In addition, the surface area of the catalyst particle measured by using nitrogen sorption is no less than 20 $m^2/g$.

Third Embodiment

The nanosized boron-containing nickel catalyst obtained from the first embodiment is placed in a reactor, such as a slurry reactor, with chloronitrobenzene, such as ortho-chloronitrobenzene, meta-chloronitrobenzene or para-chloronitrobenzene, weighted about 2.52 g and methanol of about 80 ml. In order to expel the air in the reactor, hydrogen is pumped into the reactor for 10 min. Thereafter, the mixture of the chloronitrobenzene, methanol and the nanosized boron-containing nickel catalyst in the reactor is stirred with a low stirring rate of about 100 rpm until the reaction temperature of about 40-150 centigrade is reached simultaneously with that the pressure inside the reactor is increased to the reaction pressure of about 5-40 atm. As the reaction condition is satisfied, the stirring rate is increased to 500 rpm while the reaction time t is set to be zero (t=0) and the hydrogenation process is started. Notably, during the hydrogenation process, the hydrogen is continuously supplied into the reactor to maintain the pressure inside the reactor at the reaction pressure. Furthermore, the preferred reaction pressure is of about 5-15 atm. More specifically, the most preferred reaction pressure is of about 12 atm. Furthermore, the preferred reaction temperature is about 50-120° C. More specifically, the most preferred reaction temperature is of about 120° C.

After the first ten minutes of the reaction time, about 0.5-1.0 ml solution including the reactant and the product of the hydrogenation process in the reactor is sampled. Thereafter, for every ten minutes, 0.5-1.0 ml solution including the reactant and the product of the hydrogenation process in the reactor is sampled following a step of spilling out about ten drops of the solution for excluding the sampling error. Then, after the hydrogenation process is finished, the hydrogen supply is terminated.

The sampled solution is analyzed by using gas chromatography, wherein the gas chromatography column with the length of about 3 m and the diameter of about ⅛ inches is made of stainless steel. Hence, the analyzing results are shown in following:

| Time (minutes) | 10 | 20 | 30 |
|---|---|---|---|
| p-chloronitrobenzene conversion rate (%) | 20 | 96 | 100 |
| p-chloroaniline selectivity | >99% | >99% | >99% |

Fourth Embodiment

The nanosized boron-containing nickel catalyst obtained from the first embodiment is placed in a reactor, such as a slurry reactor, with chloronitrobenzene, such as ortho-chloronitrobenzene, meta-chloronitrobenzene or para-chloronitrobenzene, weighted about 2.52 g and ethanol of about 80 ml. In order to expel the air in the reactor, hydrogen is pumped into the reactor for 10 min. Thereafter, the mixture of the chloronitrobenzene, methanol and the nanosized boron-containing nickel catalyst in the reactor is stirred with a low stirring rate of about 100 rpm until the reaction temperature of about 40-150 centigrade is reached simultaneously with that the pressure inside the reactor is increased to the reaction pressure of about 5-40 atm. As the reaction condition is satisfied, the stirring rate is increased to 500 rpm while the reaction time t is set to be zero (t=0) and the hydrogenation process is started. Notably, during the hydrogenation process, the hydrogen is continuously supplied into the reactor to maintain the pressure inside the reactor at the reaction pressure. Furthermore, the preferred reaction pressure is of about 5-15 atm. More specifically, the most preferred reaction pressure is of about 12 atm. Furthermore, the preferred reaction temperature is about 50-120° C. More specifically, the most preferred reaction temperature is of about 120° C.

After the first ten minutes of the reaction time, about 0.5-1.0 ml solution including the reactant and the product of the hydrogenation process in the reactor is sampled. Thereafter, for every ten minutes, 0.5-1.0 ml solution including the reactant and the product of the hydrogenation process in the reactor is sampled following a step of spilling out about ten drops of the solution for excluding the sampling error. Then, after the hydrogenation process is finished, the hydrogen supply is terminated.

The sampled solution is analyzed by using gas chromatography, wherein the gas chromatography column with the length of about 3 m and the diameter of about ⅛ inches is made of stainless steel. Hence, the analyzing results are shown in following:

| | Time (minutes) | | | | | | | |
|---|---|---|---|---|---|---|---|---|
| | 10 | 20 | 30 | 40 | 50 | 60 | 70 | 80 |
| p-chloronitrobenzene conversion rate (%) | 2 | 5 | 10 | 28 | 50 | 77 | 85 | 100 |
| p-chloroaniline selectivity | >99% | >99% | >99% | >99% | >99% | >99% | >99% | >99% |

Fifth Embodiment

The nanosized boron-containing nickel catalyst obtained from the second embodiment is placed in a reactor, such as a slurry reactor, with chloronitrobenzene, such as ortho-chloronitrobenzene, meta-chloronitrobenzene or para-chloronitrobenzene, weighted about 2.52 g and methanol of about 80 ml. In order to expel the air in the reactor, hydrogen is pumped into the reactor for 10 min. Thereafter, the mixture of the chloronitrobenzene, methanol and the nanosized boron-containing nickel catalyst in the reactor is stirred with a low stirring rate of about 100 rpm until the reaction temperature of about 40-150° C. is reached simultaneously with that the pressure inside the reactor is increased to the reaction pressure of about 5-40 atm. As the reaction condition is satisfied, the stirring rate is increased to 500 rpm while the reaction time t is set to be zero (t=0) and the hydrogenation process is started. Notably, during the hydrogenation process, the hydrogen is continuously supplied into the reactor to maintain the pressure inside the reactor at the reaction pressure. Furthermore, the preferred reaction pressure is of about 5-15 atm. More specifically, the most preferred reaction pressure is of about 12 atm. Furthermore, the preferred reaction temperature is about 50-120 centigrade. More specifically, the most preferred reaction temperature is of about 110° C.

After the first ten minutes of the reaction time, about 0.5-1.0 ml solution including the reactant and the product of the hydrogenation process in the reactor is sampled. Thereafter, for every ten minutes, 0.5-1.0 ml solution including the reactant and the product of the hydrogenation process in the reactor is sampled following a step of spilling out about ten drops of the solution for excluding the sampling error. Then, after the hydrogenation process is finished, the hydrogen supply is terminated.

The sampled solution is analyzed by using gas chromatography, wherein the gas chromatography column with the length of about 3 m and the diameter of about ⅛ inches is made of stainless steel. Hence, the analyzing results are shown in following:

| Time (minutes) | 10 | 20 | 30 | 40 |
|---|---|---|---|---|
| p-chloronitrobenzene conversion rate (%) | 33 | 84 | 98 | 100 |
| p-chloroaniline selectivity | >99% | >99% | >99% | >99% |

Sixth Embodiment

The nanosized boron-containing nickel catalyst obtained from the second embodiment is placed in a reactor, such as a slurry reactor, with chloronitrobenzene, such as ortho-chloronitrobenzene, meta-chloronitrobenzene or para-chloronitrobenzene, weighted about 2.52 g and methanol of about 80 ml. In order to expel the air in the reactor, hydrogen is pumped into the reactor for 10 min. Thereafter, the mixture of the chloronitrobenzene, methanol and the nanosized boron-containing nickel catalyst in the reactor is stirred with a low stirring rate of about 100 rpm until the reaction temperature of about 40-150 centigrade is reached simultaneously with that the pressure inside the reactor is increased to the reaction pressure of about 5-40 atm. As the reaction condition is satisfied, the stirring rate is increased to 500 rpm while the reaction time t is set to be zero (t=0) and the hydrogenation process is started. Notably, during the hydrogenation process, the hydrogen is continuously supplied into the reactor to maintain the pressure inside the reactor at the reaction pressure. Furthermore, the preferred reaction pressure is of about 5-15 atm. More specifically, the most preferred reaction pressure is of about 12 atm. Furthermore, the preferred reaction temperature is about 50-120° C. More specifically, the most preferred reaction temperature is of about 100° C.

After the first ten minutes of the reaction time, about 0.5-1.0 ml solution including the reactant and the product of the hydrogenation process in the reactor is sampled. Thereafter, for every ten minutes, 0.5-1.0 ml solution including the reactant and the product of the hydrogenation process in the reactor is sampled following a step of spilling out about ten drops of the solution for excluding the sampling error. Then, after the hydrogenation process is finished, the hydrogen supply is terminated.

The sampled solution is analyzed by using gas chromatography, wherein the gas chromatography column with the length of about 3 m and the diameter of about ⅛ inches is made of stainless steel. Hence, the analyzing results are shown in following:

| | Time (minutes) | | | | | |
|---|---|---|---|---|---|---|
| | 10 | 20 | 30 | 40 | 50 | 60 |
| p-chloronitrobenzene conversion rate (%) | 5 | 20 | 50 | 87 | 99 | 100 |
| p-chloroaniline selectivity | >99% | >99% | >99% | >99% | >99% | >99% |

It will be apparent to those skilled in the art that various modifications and variations can be made to the structure of the present invention without departing from the scope or spirit of the invention. In view of the foregoing descriptions, it is intended that the present invention covers modifications and variations of this invention if they fall within the scope of the following claims and their equivalents.

What is claimed is:

1. A hydrogenation process of chloronitrobenzene, comprising:
providing a nanosized boron-containing nickel catalyst, wherein a ratio of the amount of the boron atom to the amount of the nickel atom in the nanosized boron-containing nickel catalyst is of about 0.1-0.9;
placing the nanosized boron-containing nickel catalyst into a reactor with a chloronitrobenzene an alcohol solvent having carbon number less than four per molecule; and
performing a hydrogenation process to hydrogenate the chloronitrobenzene in hydrogen gas with a reaction pressure of about 5-40 atm and a reaction temperature of about 40-150° C.

2. The hydrogenation process of claim 1, wherein a method for forming the nanosized boron-containing nickel catalyst comprises a step of mixing a nickel salt and a boron hydride with the use of an ethanolic solution.

3. The hydrogenation process of claim 2, wherein the nickel salt includes at least one of nickel acetate, nickel nitrate nickel chloride and a combination thereof.

4. The hydrogenation process of claim 2, wherein the boron hydride includes at least one of potassium borohydride sodium borohydride and a combination thereof.

5. The hydrogenation process of claim 2, wherein the nanosized boron-containing nickel catalyst is formed at temperature of about 20-80° C.

6. The hydrogenation process of claim 2, wherein the formation of the nanosized boron-containing nickel catalyst is accomplished in an oxygen free environment with filling of nitrogen or hydrogen.

7. The hydrogenation process of claim 2, wherein the volume concentration of ethanol in the ethanolic solution is about 50%.

8. The hydrogenation process of claim 1, wherein the alcohol solvent includes at least one of methanol, ethanol, propanol, butanol and a combination thereof.

9. The hydrogenation process of claim 1, wherein the structure of the nanosized boron-containing nickel catalyst is amorphous type.

10. The hydrogenation process of claim 9, wherein the diameter of the particle of the nanosized boron-containing nickel catalyst is less than 50 nanometer and the surface area of the nanosized boron-containing nickel catalyst is greater than 20 $m^2/g$.

11. The hydrogenation process of claim 1, wherein the chloronitrobenzene includes at least one of para-chloronitrobenzene, meta-chloronitrobenzene ortho-chloronitrobenze and a combination thereof.

* * * * *